US008447089B2

(12) United States Patent
Liu

(10) Patent No.: US 8,447,089 B2
(45) Date of Patent: May 21, 2013

(54) SYSTEMS AND METHODS FOR SUSCEPTIBILITY TENSOR IMAGING

(76) Inventor: Chunlei Liu, Chapel Hill, NC (US)

( * ) Notice: Subject to any disclaimer, the term of this patent is extended or adjusted under 35 U.S.C. 154(b) by 149 days.

(21) Appl. No.: 13/095,200

(22) Filed: Apr. 27, 2011

(65) Prior Publication Data

US 2011/0262021 A1    Oct. 27, 2011

Related U.S. Application Data

(60) Provisional application No. 61/328,323, filed on Apr. 27, 2010.

(51) Int. Cl.
*G06K 9/00* (2006.01)
(52) U.S. Cl.
USPC ........... 382/131; 324/309; 324/318; 324/424; 600/410
(58) Field of Classification Search
USPC .... 382/131; 324/309, 307, 318, 424; 600/410
See application file for complete search history.

(56) References Cited

U.S. PATENT DOCUMENTS

| | | | |
|---|---|---|---|
| 5,539,310 | A | 7/1996 | Basser et al. |
| 6,526,305 | B1* | 2/2003 | Mori ............................ 600/410 |
| 7,319,328 | B1* | 1/2008 | Karmonik ..................... 324/318 |
| 7,348,776 | B1 | 3/2008 | Aksoy et al. |
| 7,408,345 | B2 | 8/2008 | Bammer et al. |
| 7,612,561 | B2* | 11/2009 | Tatebayashi et al. ......... 324/318 |
| 2003/0212322 | A1 | 11/2003 | Haacke |
| 2003/0214289 | A1* | 11/2003 | van Muiswinkel et al. .. 324/307 |
| 2005/0101857 | A1* | 5/2005 | Masutani et al. ............. 600/410 |
| 2006/0170422 | A1* | 8/2006 | Hornung ....................... 324/318 |
| 2006/0229856 | A1* | 10/2006 | Burrus et al. ................... 703/11 |
| 2006/0281987 | A1* | 12/2006 | Bartesaghi et al. ........... 600/410 |
| 2007/0297660 | A1* | 12/2007 | Hsieh et al. ................... 382/131 |
| 2008/0205733 | A1* | 8/2008 | Laidlaw et al. ............... 382/131 |
| 2008/0284434 | A1 | 11/2008 | Wedeen |
| 2009/0118608 | A1* | 5/2009 | Koay ............................. 600/410 |
| 2010/0004527 | A1* | 1/2010 | Dale et al. ..................... 600/410 |

(Continued)

FOREIGN PATENT DOCUMENTS

| WO | WO01-38895 | A1 | 5/2001 |
|---|---|---|---|
| WO | WO0138895 | A1 | 5/2001 |
| WO | WO2011/139745 | A1 | 11/2011 |

OTHER PUBLICATIONS

Elias R. Melhem; Susumu Mori; Govind Mukundan; Michael A. Kraut; Martin G. Pomper; Peter C. M. van Zij;,"Diffusion tensor MR imaging of brain and white matter tractography",American Roentgen ray Society, AJR:178,Jan. 2002.*

(Continued)

*Primary Examiner* — Stephen R Koziol
*Assistant Examiner* — Shaghayegh Azima
(74) *Attorney, Agent, or Firm* — Olive Law Group, PLLC

(57) ABSTRACT

The present disclosure provides a method and system for quantifying and making images of tissue anisotropy property based on magnetic resonance imaging (MRI). The systems and methods provided herein utilize orientation distribution of magnetic susceptibility to characterize magnetic susceptibility anisotropy (MSA) inside biological tissues. This MSA may be intrinsic property of the tissue or may be induced by the presence of external agents. In certain embodiments, the MSA is displayed as an orientation distribution function of susceptibility and/or may be described by mathematical quantities such as tensors (e.g., symmetric or asymmetric second order or higher order tensors) and spherical harmonics. In other embodiments, the MSA is characterized using a second order tensor named apparent susceptibility tensor (AST).

19 Claims, 15 Drawing Sheets

U.S. PATENT DOCUMENTS

2010/0079456 A1\* 4/2010 Barth .......................... 345/424
2010/0142785 A1\* 6/2010 Dahnke et al. ................ 382/131
2010/0259261 A1\* 10/2010 Saes et al. .................... 324/309
2011/0044524 A1\* 2/2011 Wang et al. ................... 382/131

OTHER PUBLICATIONS

C.-F. Westi;, S.E. Maier; H. Mamata, A. Nabavi; F.A. Jolesz; R. Kikinis;,"Processing and visualization of diffusion tensor MRI", Medical Image analysis, Elsevier, 2002.\*

Int'l. Search Rpt. for PCT/US2011/034086 mailed Nov. 16, 2011.

Notification of Transmittal of the International Search Report and the Written Opinion of the International Searching Authority, or the Declaration, for corresponding PCT International Application No. PCT/US2011/034086, Korean Intellectual Property Office, Nov. 11, 2011; references included herein.

Related U.S. Appl. No. 13/517,633, filed Jun. 14, 2012, not yet published.

Related Int'l. Patent Application No. PCT/US2012/042337 filed Jun. 14, 2012, not yet published.

\* cited by examiner

SYSTEMS AND METHODS FOR SUSCEPTIBILITY TENSOR IMAGING

CROSS-REFERENCE TO RELATED APPLICATION

This application claims priority to U.S. Provisional Patent Application No. 61/328,323 filed on Apr. 27, 2010, the entire content of which is hereby incorporated by reference.

GOVERNMENT INTEREST

The present disclosure was made with U.S. Government support under the following grants: NIH/NIBIB Grant No. 4R00 EB007182-03. Accordingly, the Federal Government has rights to this invention.

TECHNICAL FIELD

The present disclosure relates to systems and methods for quantifying and generating images of tissue anisotropy property based in magnetic resonance imaging (MRI).

BACKGROUND

Magnetic resonance imaging (MRI) is a non-destructive method for the analysis of materials and represents a new approach to medical imaging. It is generally non-invasive and does not involve ionizing radiation. In very general terms, nuclear magnetic moments are excited at specific spin precession frequencies which are proportional to the local magnetic field. The radio-frequency signals resulting from the precession of these spins are received using pickup coils. By manipulating the magnetic fields, an array of signals is provided representing different regions of the volume. These are combined to produce a volumetric image of the nuclear spin density of the body.

MRI signals for reconstructing an image of an object are obtained by placing the object in a magnetic field, applying magnetic gradients for slice selection, applying a magnetic excitation pulse to tilt nuclei spins in the desired slice or volume, and then detecting MRI signals emitted from the tilted nuclei spins while applying readout gradients. The detected signals may be envisioned as traversing lines in a Fourier transformed space (k-space) with the lines aligned and spaced parallel in Cartesian trajectories or emanating from the origin of k-space in spiral trajectories.

An MRI may be used for scanning a patient's brain. The MRI may be useful for measuring development of the brain, particularly for scanning white-matter within the brain. White matter is a component of the central nervous system and consists of myelinated axons. Myelin acts as an insulator around nerve cells and increases the speed of transmission of nerve signals. The multilayered myelin sheath wrapping around nerve axons is essential for proper functioning of the central nervous system. Abnormal myelination leads to a wide range of neurological diseases and developmental disorders. MRI is the preferred reference test for diagnosing and monitoring the evolution of white-matter development and related diseases due to its excellent soft tissue contrast, high spatial resolution, and non-radioactive nature. However, conventional MRI methods may not provide satisfactory accuracy for quantifying the myelinated axons, and determining, for example, the amount of myelinated axons present in a subject's brain.

SUMMARY

According to one embodiment, a method for magnetic resonance imaging (MRI) is provided. The method includes using an MRI system to acquire imaging data of an object. The imaging data includes a plurality of voxels. The method includes determining orientations of the voxels. The method includes generating an image based on the orientations of the voxels for depicting a characteristic of the object.

According to one embodiment, using an MRI system includes using the MRI system to apply a magnetic field to the object.

According to one embodiment, using an MRI system includes using the MRI system to acquire imaging data of the object at a plurality of orientations of the object relative to a magnetic field generated by the MRI system.

According to one embodiment, determining orientations of the voxels includes determining magnetic susceptibility tensors of the voxels.

According to one embodiment, determining one of vector components, eigenvalue decomposition, and invariant functions of susceptibility tensors of the voxels, and generating an image includes generating the image based on the one of vector components, eigenvalue decomposition, and invariant functions of the susceptibility tensors.

According to one embodiment, a method includes determining whether each of the voxels has an eigenvalue greater than a predetermined magnitude. A method includes identifying adjacent voxels that each have an eigenvalue greater than the predetermined magnitude. For each identified adjacent voxel, the method includes determining whether an angle between eigenvectors of the identified adjacent voxels is less than a predetermined angle value. The method includes generating an image that depicts one or more lines extending between the identified adjacent voxels in which the angle between eigenvectors is less than the predetermined angle value.

According to one embodiment, a method includes generating an image based on the magnetic susceptibility tensors for depicting a tissue characteristic of the object.

According to one embodiment, a method includes determining whether an angle between orientations of adjacent voxels is less than a predetermined angle value generating an image that depicts one or more lines extending between the adjacent voxels in which the angle is less than the predetermined angle value.

According to one embodiment, a method includes determining apparent susceptibility tensors of the voxels.

According to one embodiment, a method includes determining a distribution function of the voxels.

According to one embodiment, the object includes a fiber structure, and a method includes identifying a set of voxels corresponding to the fiber structure based on one of magnetic susceptibility and resonance frequency shift of the set of voxels.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Further, the claimed subject matter is not limited to implementations that solve any or all disadvantages noted in any part of this disclosure.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings.

DETAILED DESCRIPTION

The presently disclosed subject matter now will be described more fully hereinafter with reference to the accompanying drawings, in which some, but not all embodiments are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 1:
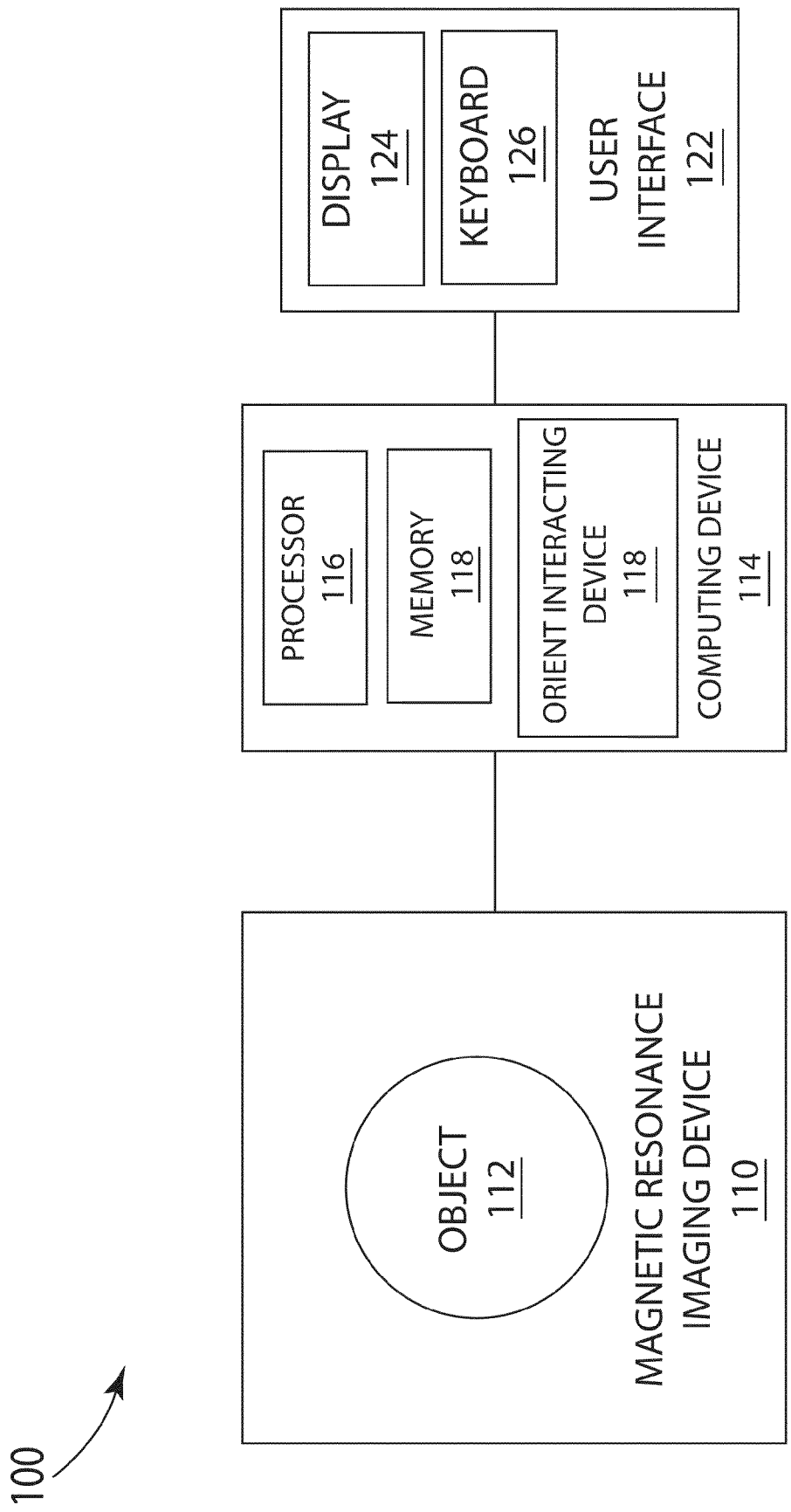
FIG. 1 is a block diagram of a magnetic resonance imaging (MRI) system according to embodiments of the present invention.

FIG. 1 illustrates a block diagram of a magnetic resonance imaging (MRI) system 100 according to one or more embodiments disclosed herein. The system 100 may include an MRI device 110. The MRI device 110 may be configured for scanning and capturing an image of an object 112 such as an anatomical image of an object. The MRI system 100 may include a computing device 114. The computing device 114 may include a processor 116, a memory 118, and an object interacting application 120 that is configured to execute on the processor 116. The MRI system 110 may include a user-interface 122, such as an image generator, that is configured for displaying images on a display 124 and receiving user-input through a user-input device, such as, for example, a keyboard 126.

Figure 2:
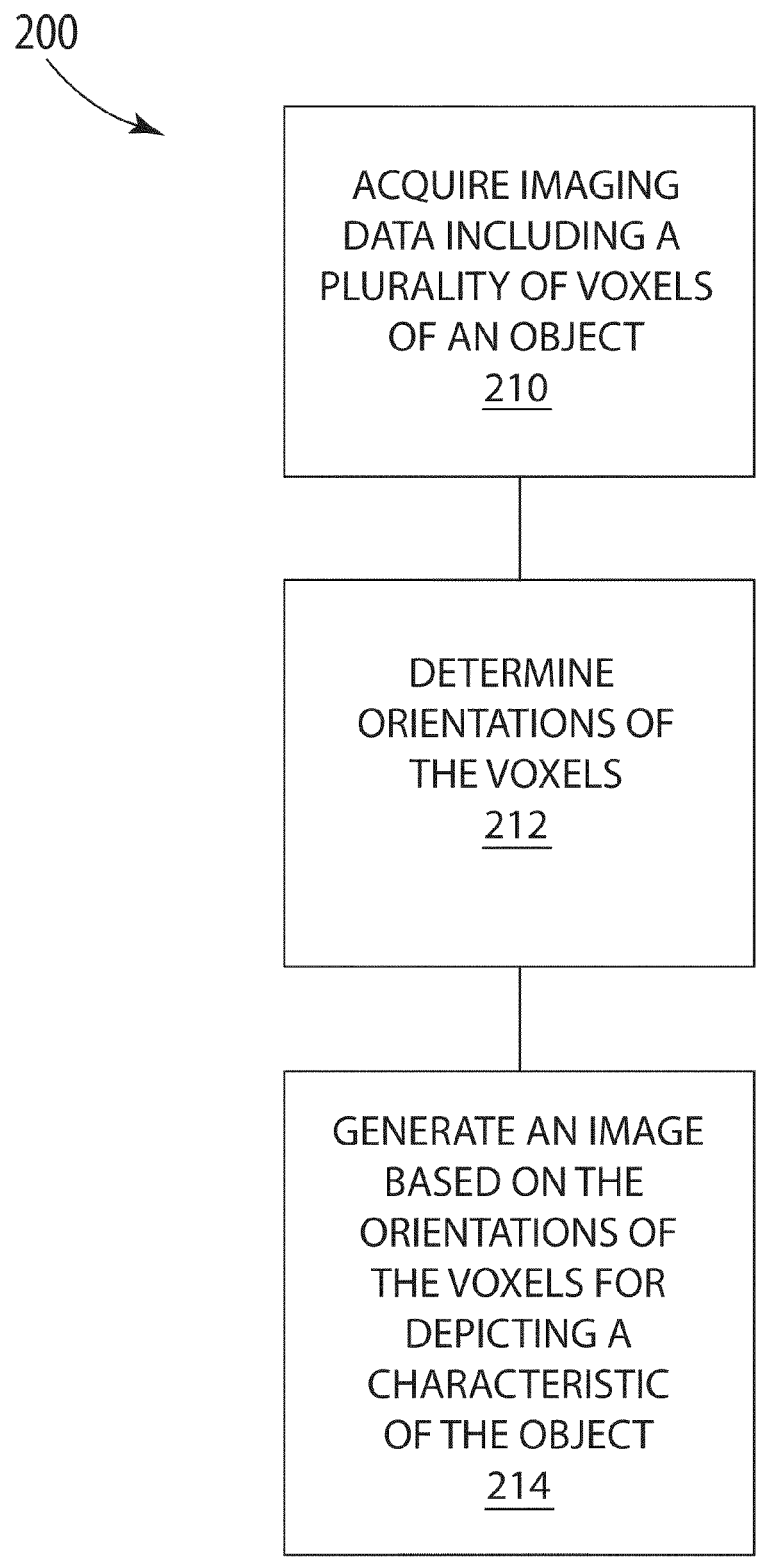
FIG. 2 is a flowchart of a method for MRI in accordance with embodiments of the present invention.

FIG. 2 illustrates a flowchart of a method for magnetic resonance imaging 200 in accordance with one or more embodiments of the present invention. The method of FIG. 2 is described as being implemented by the MRI system 100 shown in FIG. 1; however, this example method should not be considered so limiting as the method may be applied to any suitable MRI system or other imaging system. Referring to FIG. 2, the method 200 may include acquiring image data of an object 202. The image data may include, for example, 3-D spatial information, gradients, and any other desired image data. In one or more embodiments, the image data may include one or more voxels. The imaging data may be acquired using an MRI system, such as system 100, to apply a magnetic field to the object. The imaging data may be acquired at multiple data points, including, for example, acquiring imaging data of the object at a plurality of orientations of the object relative to a magnetic field generated by the MRI system. The imaging data may also be acquired with, for example, a gradient-echo or similar sequence.

The method 200 may include determining an orientation of one or more voxels 204. For example, the one or more orientations may also be an apparent susceptibility tensor. In other embodiments, the one or more orientations may be a magnetic susceptibility tensor. In other embodiments, the one or more orientations may be an orientation distribution function (ODF) of susceptibility.

The method 200 may include generating an image based on the orientation of the voxels for depicting a characteristic of the object 206. The characteristic may be, for example, the presence of adjacent voxels having sufficiently similar orientations that may be representative of, for example, white matter within a brain of a patient.

Figure 9:
FIG. 9 is an illustration of a major susceptibility vector projected onto an FSA map in accordance with embodiments of the present invention.
Figure 10:
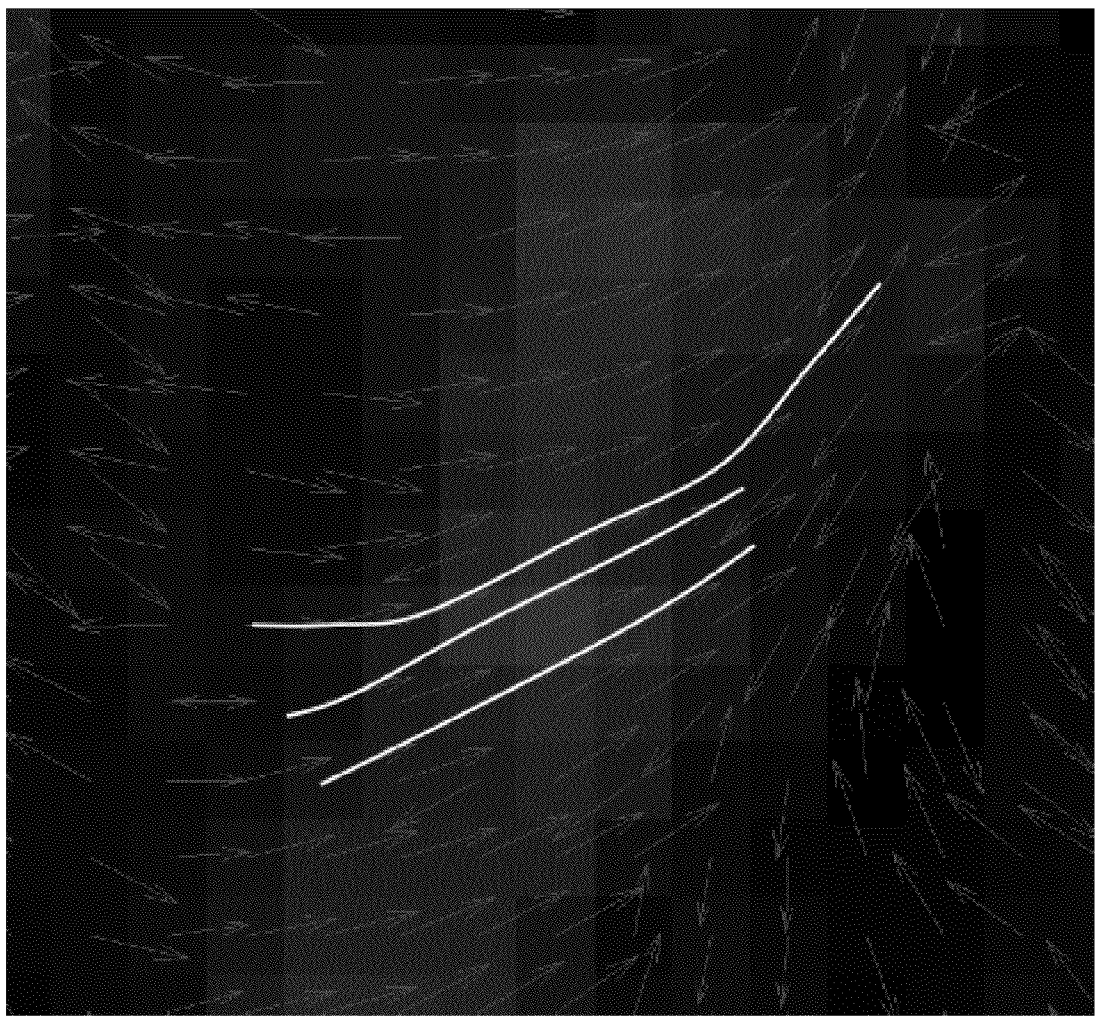
FIG. 10 is an illustration of a fiber reconstruction based on STI in accordance with embodiments of the present invention.
Figure 11:
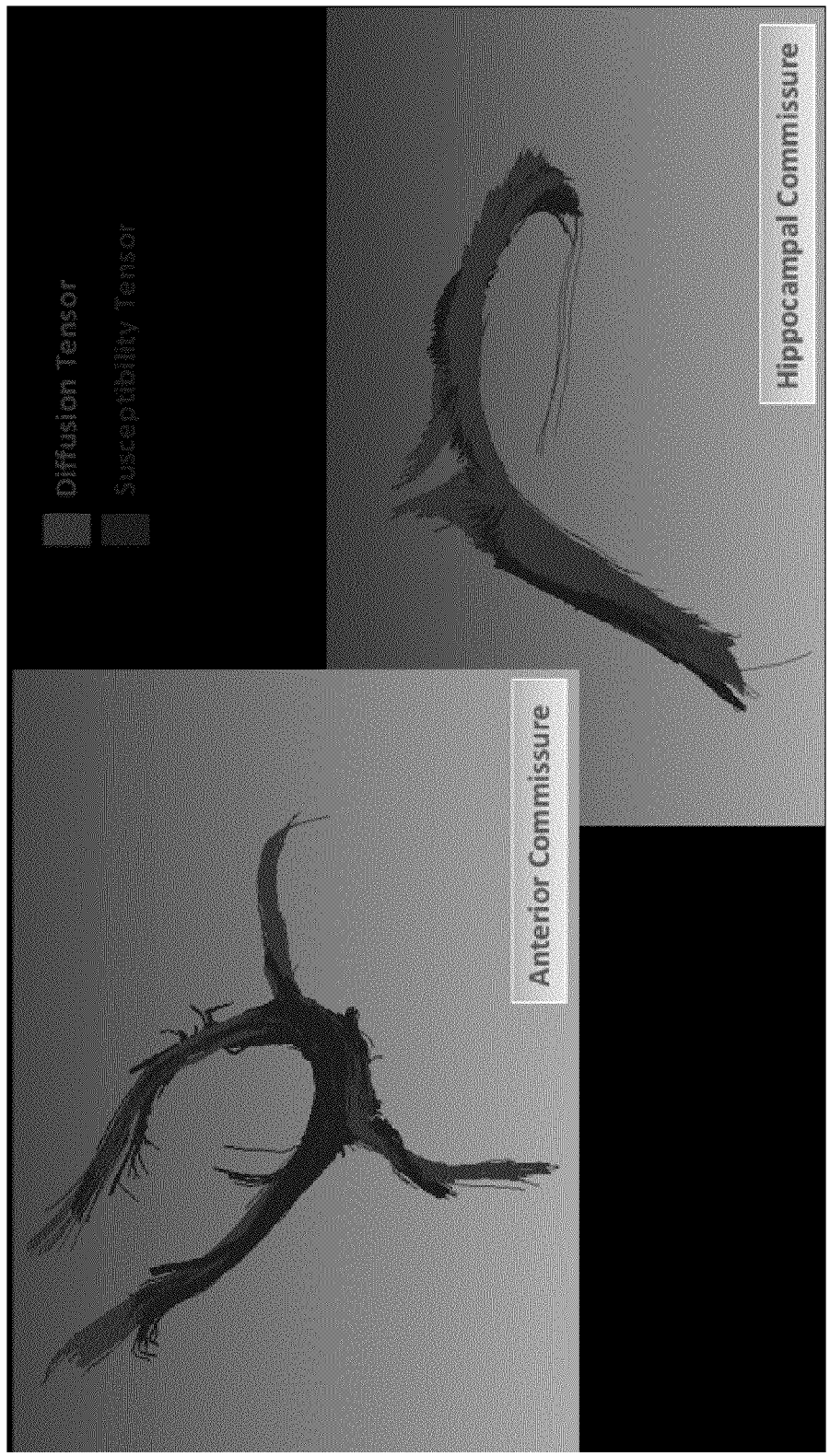
FIG. 11 is an illustration of a comparison of DTI fiber tracking and STI fiber tracking in the anterior commissure and the hippocampal commissure in accordance with embodiments of the present invention.

A method may include generating an image for voxels whose major eigen-value or FSA is above a predetermined value. For each chosen voxel, the method may include determining the fiber orientation based on the major eigen-vector orientation or orientation distribution function (ODF). A method may also include plotting a line between adjacent voxels. In one or more embodiments, a line may be plotted between adjacent voxels if the angle between the two major eigenvectors is smaller than a predetermined value. As an example, FIG. 10 illustrates this procedure for a region of interest (ROI) chosen from FIG. 9.

An example method may include determining one of vector components, eigenvalue decomposition, and/or invariant functions of susceptibility tensors of each of the voxels. The method may include generating an image based on the one of the vector components, eigenvalue decomposition, and/or invariant functions of the susceptibility tensors, or combinations thereof.

Another example method may include determining whether each of the voxels has an eigenvalue greater than a predetermined magnitude. A method may also include identifying adjacent voxels that each have an eigenvalue greater than the predetermined magnitude. For each identified adjacent voxel, a method may include determining whether an angle between eigenvectors of the identified adjacent voxels is less than a predetermined angle value. For each identified adjacent voxel, a method may include determining whether an angle between orientations of adjacent voxels is less than a predetermined angle value. Another example method may also include generating an image that depicts one or more lines extending between the identified adjacent voxels in which the angle between eigenvectors is less than the predetermined angle value.

Yet another example method may include generating an image based on the magnetic susceptibility tensors for depicting a tissue characteristic of the object. The tissue characteristic may be, for example, the presence of white matter such as myelinated axons. A method may include identifying a set of voxels corresponding to the fiber structure based on one of magnetic susceptibility and resonance frequency shift of the set of voxels Apparent Susceptibility Tensor One manner of determining an orientation of one or more voxels 204 may include determining an apparent susceptibility tensor (AST). If it is assumed that the anisotropic susceptibility, that is the directional susceptibility of an object, is described by a second-order (or rank 2) tensor $\chi$ that is referred to as the apparent susceptibility tensor (AST), then the magnetic flux density vector B relative to each nucleus is related to the macroscopic flux density $B_0$ as:

$$B_i = (\delta_{ij} - \sigma\delta_{ij} - 2/3\chi_{ij})B_{0j} \quad [1]$$

with the further assumption that the nucleus is situated within a small sphere of Lorentz. $B_i$ is the i-th component of vector B; $B_{0j}$ is the j-th component of vector $B_0$; $\delta_{ij}$ is the Kronecker delta function; and $\sigma$ is the chemical shift caused by an electronic screen effect. The vacuum permeability $\mu_0$ is assumed to be one for simplicity. The macroscopic flux density $B_0$ is further related to the applied magnetic field vector H and the demagnetizing field h as:

$$B_{0i} = (+\delta_{ij}\chi_{ij})(-H_j h_j) \quad [2]$$

The demagnetizing field is a result of the loading of objects into the scanner and is generated in order to satisfy Maxwell's equations. For modern superconductor MRI scanners, h<<H. For biological samples that are MRI compatible, it can also be assumed that the magnitude of susceptibility is small such that $\chi_{ij}$<<1. Substituting Eq. [2] into Eq. [1] and keeping only up to the first-order terms, obtains:

$$B_i = (\delta_{ij} - \sigma\delta_{ij} + 1/3\chi_{ij})(H_j + h_j) \quad [3]$$

To determine the demagnetizing field, the divergence of the flux density is zero from Maxwell's equation:

$$\nabla_i B_i = 0 \quad [4]$$

In the absence of loading, Eq. [4] is also satisfied, which results in:

$$\nabla_i H_i = 0 \quad [5]$$

Combining Eqs. [3], [4] and [5] while keeping terms only up to the first order, obtains:

$$H_j \nabla_i \chi_{ij} + \nabla_i h_i = 0 \quad [6]$$

To facilitate calculation, a scalar magnetic potential $\Phi$ is defined such that:

$$h = -\nabla\Phi \quad [7]$$

Substituting Eq. [7] to Eq. [6], obtains:

$$\nabla^2 \Phi = H_{ji} \overline{\chi}_{ij} \quad [8]$$

Eq. [8] may be solved in the spatial frequency domain. The solution expressed in the forms of Fourier transform becomes:

$$\Phi = FT^{-1}\left\{i\frac{k_i H_j}{2\pi k^2} FT\{\chi_{ij}\}\right\} \quad [9]$$

Here, $k_i$ is the i-th axis in the frequency domain and $k^2 = k_1^2 + k_2^2 + k_3^2$. FT and $FT^1$ represent the forward and inverse Fourier transform operators respectively. Substituting Eq. [9] into Eq. [7], obtains the formula for demagnetizing field flux density as:

$$h_i = -FT^{-1}\left\{k_i \frac{k_{j'} H_{j'}}{k^2} FT\{\chi_{i'j'}\}\right\} \quad [10]$$

MR Observable Field

The magnetic flux density seen by the nucleus may be found by substituting Eq. [10] into Eq. [3]. By keeping terms up to the first order, it may be simplified to:

$$B_i = (1-\sigma)H_i + FT^{-1}\left\{\frac{1}{3}H_j FT\{\chi_{ij}\} - k_i \frac{k_{j'} H_{j'}}{k^2} FT\{\chi_{i'j'}\}\right\} \quad [11]$$

If the reference is set to be $(1-\sigma)H_i$, then the off-resonance field b may be expressed as:

$$b_i = FT^{-1}\left\{\frac{1}{3}H_j FT\{\chi_{ij}\} - k_i \frac{k_{j'} H_{j'}}{k^2} FT\{\chi_{i'j'}\}\right\} \quad [12]$$

In MRI, what is observed is signal phase instead of the full vector b. The observable phase in the subject frame of reference may be expressed as:

$$\theta = \gamma t b_i \hat{H}_i = FT^{-1}\left\{\frac{1}{3}\hat{H}_i \hat{H}_j FT\{\chi_{ij}\} - k_i \hat{H}_i \frac{k_{j'} \hat{H}_{j'}}{k^2} FT\{\chi_{i'j'}\}\right\}\gamma H_0 t \quad [13.a]$$

In the laboratory frame of reference, this is expressed as:

$$\theta = \gamma t b_3 \hat{H}_3 = FT^{-1}\left\{\frac{1}{3}FT\{\chi_{33}\} - \frac{k_3 k_{j'}}{k^2} FT\{\chi_{i'3}\}\right\}\gamma H_0 t \quad [13.b]$$

Here, $H_0$ is the magnitude of the applied magnetic field; $\hat{H}_i$ is the unit vector along the i-th axis; and t is the time of echo (TE) in a gradient echo sequence. If a sufficient number of independent measurements are available, Eq. [13] may be inverted to determine $\chi$. Either frame of reference may be used in calculating the magnetic susceptibility tensor.

Determination of AST

AST may be determined by several methods or techniques as disclosed herein. In one example method, AST may be measured by rotating the subject inside the magnet and by acquiring an image at each orientation. In another method, AST may be measured by rotating the main magnetic field if permitted. In another method, AST may be measured by acquiring a spectrum of dipole coupling and through nonlinear estimation. As an example, the method of rotating the subject inside the magnet and acquiring an image at each orientation is demonstrated for its relative convenience.

Assuming that AST is a symmetric tensor, then there are six independent variables to be determined for each tensor. In principle, six independent measurements are necessary that may be acquired with different relative orientations between the object and main magnetic field. Additional symmetry may be imposed, for example, by assuming $\lambda_2 = \lambda_3$. Independent measurements may be obtained by rotating the imaging object with respect to the main magnetic field. Given a set of measurements, an AST may be estimated by inverting the system of linear equations formed by Eq. [13.a] in the subject frame of reference or Eq. [13.b] in the laboratory-frame of reference. When solving Eq. [13], regularization terms may be added and iterative steps may be applied, for example, to improve accuracy and reduce artifacts.

Subject-Frame of Reference

For a subject-frame approach, images at different orientations will be first co-registered to a chosen reference orientation. The six rigid-body transformation parameters may be estimated using only magnitude images. The estimated transformation matrix may be used to register and re-slice the real and imaginary part separately. Phase maps may be computed from the registered real and imaginary parts. Once all phase maps are computed and preprocessed, AST may be computed for each voxel. Specifically, by taking Fourier transform of both sides of Eq. [13.a], Eq. [13.a] is rewritten as:

$$FT\{\tilde{\theta}\} = \left(\frac{1}{3}\hat{H}_{i'}\hat{H}_{j'} - k_i\hat{H}_i\frac{k_{j'}\hat{H}_{j'}}{k^2}\right)FT\{\chi_{i'j'}\} \quad [14]$$

Here, $\tilde{\theta}$ is the normalized phase according to:

$$\tilde{\theta} = \frac{\theta}{\gamma H_0 t} \quad [15]$$

Given a set of n measurements, a measurement vector $\tilde{\theta}$, a vector of unknowns x and a system matrix A may be defined in the frequency domain:

$$\tilde{\theta} = [\tilde{\theta}_1(k) \ \tilde{\theta}_2(k) \ \ldots \ \tilde{\theta}_n(k)]^T \quad [16]$$

$$x = [\chi_{11}(k) \ \chi_{12}(k) \ \chi_{13}(k) \ \chi_{22}(k) \ \chi_{23}(k) \ \chi_{33}(k)]^T \quad [17]$$

$$A = \begin{bmatrix} \frac{1}{3}\hat{H}_1^{(1)}\hat{H}_1^{(1)} - & \frac{2}{3}\hat{H}_1^{(1)}\hat{H}_2^{(1)} - & \ldots & \frac{1}{3}\hat{H}_3^{(1)}\hat{H}_3^{(1)} - \\ k_i\hat{H}_i^{(1)}\frac{k_1\hat{H}_1^{(1)}}{k^2} & k_i\hat{H}_i^{(1)}\frac{k_1\hat{H}_2^{(1)}+k_2\hat{H}_1^{(1)}}{k^2} & & k_i\hat{H}_i^{(1)}\frac{k_3\hat{H}_3^{(1)}}{k^2} \\ \frac{1}{3}\hat{H}_1^{(2)}\hat{H}_1^{(2)} - & \frac{2}{3}\hat{H}_1^{(2)}\hat{H}_2^{(2)} - & \ldots & \frac{1}{3}\hat{H}_3^{(2)}\hat{H}_3^{(2)} - \\ k_i\hat{H}_i^{(2)}\frac{k_1\hat{H}_1^{(2)}}{k^2} & k_i\hat{H}_i^{(2)}\frac{k_1\hat{H}_2^{(2)}+k_2\hat{H}_1^{(2)}}{k^2} & & k_i\hat{H}_i^{(2)}\frac{k_3\hat{H}_3^{(2)}}{k^2} \\ \vdots & \vdots & \vdots & \vdots \\ \frac{1}{3}\hat{H}_1^{(n)}\hat{H}_1^{(n)} - & \frac{2}{3}\hat{H}_1^{(n)}\hat{H}_2^{(n)} - & \ldots & \frac{1}{3}\hat{H}_3^{(n)}\hat{H}_3^{(n)} - \\ k_i\hat{H}_i^{(n)}\frac{k_1\hat{H}_1^{(n)}}{k^2} & k_i\hat{H}_i^{(n)}\frac{k_1\hat{H}_2^{(n)}+k_2\hat{H}_1^{(n)}}{k^2} & & k_i\hat{H}_i^{(n)}\frac{k_3\hat{H}_3^{(n)}}{k^2} \end{bmatrix} \quad [18]$$

The resultant system of linear equations may be solved for each voxel using least-squares estimation as:

$$x = (A^T A)\tilde{\theta}^{-1} A^T \quad [19]$$

Once x is computed for each voxel, the entries of AST may be computed through a 3D inverse Fourier transform.

Laboratory-Frame of Reference

For a laboratory-frame based approach, an apparent magnetic susceptibility (AMS) may be computed for each orientation. The computed AMS map can then be registered to the reference orientation using the same transformation parameters obtained via magnitude image registration. The AMS ($\chi_{33}'$) of a given voxel on the spatially registered AMS map may be expressed in terms of the underlying true AST ($\chi$) as:

$$\chi_{33}' = R_3^T \chi R \quad [20]$$

Here, R is the 3D rotation matrix that transforms an image volume to match a reference. The rotation matrix may be decomposed into three basic rotation matrixes as:

$$R = R_x R_y R_z \quad [21]$$

The three basic rotation matrix are given by:

$$R_x(\alpha) = \begin{bmatrix} 1 & 0 & 0 \\ 0 & \cos\alpha & \sin\alpha \\ 0 & -\sin\alpha & \cos\alpha \end{bmatrix} \quad [22]$$

$$R_y(\beta) = \begin{bmatrix} \cos\beta & 0 & -\sin\beta \\ 0 & 1 & 0 \\ \sin\beta & 0 & \cos\beta \end{bmatrix} \quad [23]$$

$$R_z(\gamma) = \begin{bmatrix} \cos\gamma & \sin\gamma & 0 \\ -\sin\gamma & \cos\gamma & 0 \\ 0 & 0 & 1 \end{bmatrix} \quad [24]$$

There is one rotation matrix R for each imaging volume. Once all AMS maps are registered, the underlying AST can then be estimated by inverting the resultant system of linear equation for each voxel. More specifically, b is defined as a vector of AMS measured at n different orientation, a vector unknown x and a system matrix B:

$$b = [\chi_{33}'^{(1)} \ \chi_{33}'^{(2)} \ \ldots \ \chi_{33}'^{(n)}]^T \quad [25]$$

$$x = [x_{11}(r) \ x_{12}(r) \ x_{13}(r) \ x_{22}(r) \ x_{23}(r) \ x_{33}(r)]^T \quad [26]$$

$$B = \begin{bmatrix} R_{13}^{(1)}R_{13}^{(1)} & 2R_{13}^{(1)}R_{23}^{(1)} & \ldots & R_{33}^{(1)}R_{33}^{(1)} \\ R_{13}^{(2)}R_{13}^{(2)} & 2R_{13}^{(2)}R_{23}^{(2)} & \ldots & R_{33}^{(2)}R_{33}^{(2)} \\ \vdots & \vdots & \vdots & \vdots \\ R_{13}^{(n)}R_{13}^{(n)} & R_{13}^{(n)}R_{23}^{(n)} & \ldots & R_{33}^{(n)}R_{33}^{(n)} \end{bmatrix} \quad [27]$$

Here, the number in the parentheses of the upper index enumerates the number of orientations sampled. The difference between Eq. [26] and Eq. [17] is that Eq. [26] is expressed in the image domain while Eq. [17] is expressed in the frequency domain. Once the three notations are defined, the AST in the image domain may be found for each voxel as:

$$x = (B^T B)^{-1} B^T b \quad [28]$$

Setting Baseline Reference

Figure 3A:
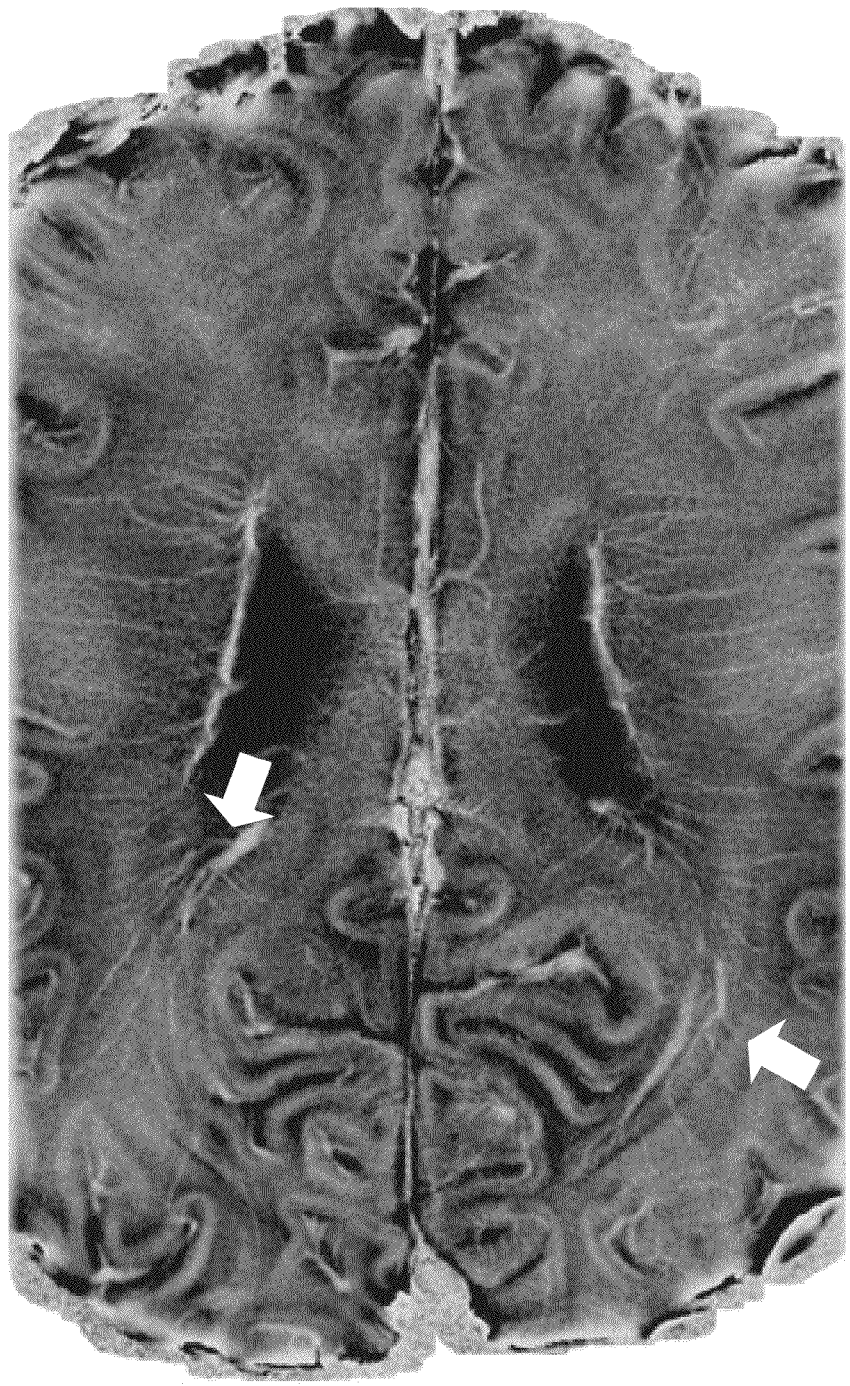
FIGS. 3A and 3B are an illustration of in-vivo MRI images of a human brain in accordance with the present invention.
Figure 3B:
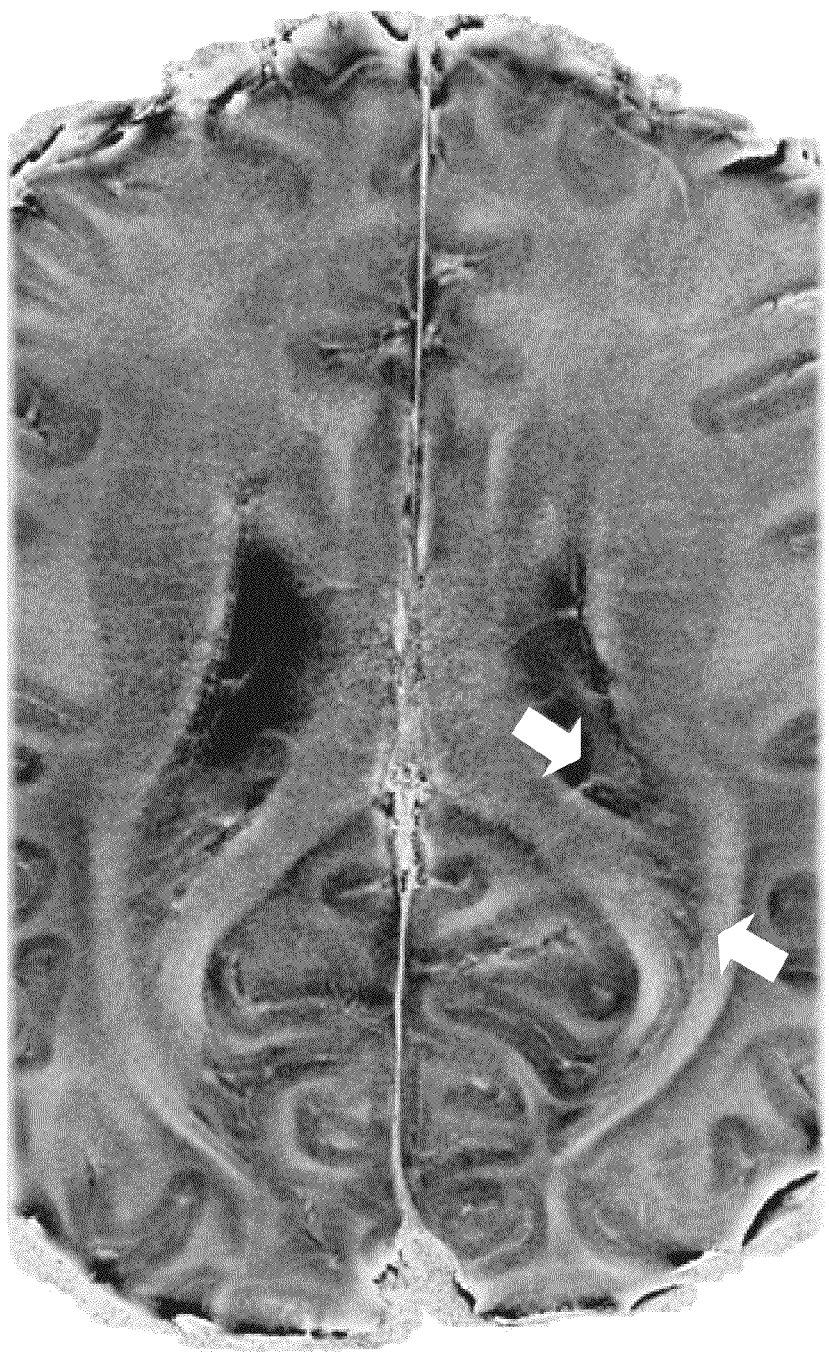

An uncertainty in phase images may be induced by, for example, receiver phase and the choice of reference frequency. In addition, subtle phase contrast may be disguised or overwhelmed by the presence of large local susceptibility such as bone and air. For images acquired with multiple-channel receiver coil, a complex-valued image may be reconstructed for each channel of the coil. A low-resolution phase map may be extracted from each coil by low-pass filtering the phase map with a Fermi filter or by fitting with a smooth polynomial or spline-type function or by Laplace filtering. This low-resolution phase is then subtracted from each coil. After removing global phases, images from all coils are combined in complex numbers to form the final image. To ensure that all images have a common reference, a uniform reference marker may be inserted in the coil, imaged at each session and served as a reference. Alternatively, an internal reference location can also be chosen as a reference such as the cerebral spinal fluid (CSF). Given a reference point, phase at other locations may be either positive or negative. FIGS. 3A and 3B show the intensity-reversed phase sensitive images (RPSI) created by weighing the magnitude image by the negative and positive phase respectively. Here, negative phase tends to highlight vessels due to flow and the presence of iron whereas positive phase highlights the minute structure within white matter.

Setting the reference consistently addresses several important issues in quantifying AST such as a baseline shift that affects the mean susceptibility and a potential change of anisotropy caused by the baseline inconsistency in AMS or in the phase maps. The first effect is less significant as a constant shift in all AMS results in an addition of an identity matrix to the original AST and therefore does not affect the anisotropy:

$$R_\chi^T(+I\delta R)R \chi R I\delta \qquad [29]$$

The internal reference chosen may contain anisotropic susceptibility, although it is expected to be small inside CSF. If the reference region of interest (ROI) indeed has intrinsic magnetic susceptibility anisotropy ("MSA"), then the AST of the reference ROI will be subtracted from all voxels and therefore not affect the overall MSA contrast of the whole image volume.

Solving Eq. [14] is complicated when the image phase is wrapped around $2\pi$. Phase wrapping appears commonly in high field imaging especially when large off-resonance is present and when TE is relatively large. The uncertainty in wrapped phase, if uncorrected, results in large errors in the estimated AST. A common approach in calculating susceptibility from phase images is to perform a phase unwrapping procedure prior to the matrix inversion. There are a number of algorithms existing in the literature for phase unwrapping. However, performing phase unwrapping for the calculation of AST is, unfortunately, not a feasible solution because of the uncertainty in the baseline phase. When performing phase unwrapping, a region has to be chosen as the reference. When different references are chosen, the unwrapped phase may be offset by multiples of $2\pi$. It is improbable to assure that the unwrapped phases are consistent among different orientations even if the same reference region is used, because phase changes when the object orients differently with respect to the main magnetic field.

An example solution to this problem, according to at least one embodiment of the invention, may involve several steps described hereinafter. In an example step, the Laplacian of the phase is computed using only cosine and sine functions of the phase which is, thus, indifferent to the phase wrapping issue. In another example step, once the Laplacian is computed, the Fourier transform of the phase is computed through the Fourier transform of the Laplacian. In another example step, a phase map is multiplied by a mask, such as 1 inside the brain and zero outside, and the Laplacian operator is applied for a second time. This process may be iterated. Specifically, the Laplacian of the phase image is computed using the following trigonometric relationship:

$$\nabla^2 \theta = \cos\theta^2 \nabla n\theta s + \theta^2 \nabla \delta s\theta \qquad [30]$$

Furthermore, the Laplacian of the trigonometric functions may be computed via Fourier transform as:

$$\nabla^2 s\text{in}\,\theta = (2\pi)^2 FT^{-1}\{k^2 FT\{\sin\theta\}\} \qquad [31]$$

$$\nabla^2 c\text{os}\,\theta = (2\pi)^2 FT^{-1}\{k^2 FT\{\cos\theta\}\} \qquad [32]$$

Once the Laplacian is computed, the Fourier transform of the phase image (the left side of Eq. [14]) can then be computed as:

$$FT\{\theta\} = -\frac{1}{4\pi^2}\frac{1}{k^2}FT\{\nabla^2\theta\} \qquad [33]$$

In the numerical implementation of this approach, a small number ($1.0\times10^{-9}$) is added to $k^2$ in the denominator to avoid dividing by zero. In addition, the Laplacians are computed on a matrix that is twice the size of the original image. In expanding the size of the matrix, the original phase image is mirrored to different quadrants, creating an even function, which, therefore, guarantees the computed Laplacian to be real. A further advantage of this method is that the background phase is automatically removed once the Laplacian is operated on masked phase maps. The mask may be generated based on the magnitude image which defines the interior of the brain (or region of interest) and exterior.

Quantifying MSA

The computed AST is coordinate system dependent. To define rotational invariant quantities, eigen-value decomposition of the AST is performed and three principal susceptibilities are defined. The three principal susceptibilities are denoted as $\chi_1$, $\chi_2$, and $\chi_3$, ranked in a descending order. There is also an eigen-vector corresponding to each principal susceptibility. The major eigen-vector points towards the direction that exhibits the largest magnetic susceptibility. Fractional susceptibility anisotropy (FSA) is defined to quantitatively characterize anisotropy observed in susceptibility as:

$$FSA = \sqrt{\frac{3((\chi_1-\bar{\chi})^2 + (\chi_2-\bar{\chi})^2 + (\chi_3-\bar{\chi})^2)}{2(\chi_1^2+\chi_2^2+\chi_3^2)}} \qquad [34.a]$$

where $\bar{\chi}$ is the mean susceptibility. Eigen-decomposition also provides three eigen-vectors that define the orientation of the three principal susceptibilities.

Alternatively, MSA may be defined as:

$$MSA = \chi_1 - \frac{\chi_2+\chi_3}{2} \qquad [34.b]$$

An example advantage of this definition is that it is indifferent to the reference frequency.

Figure 4:
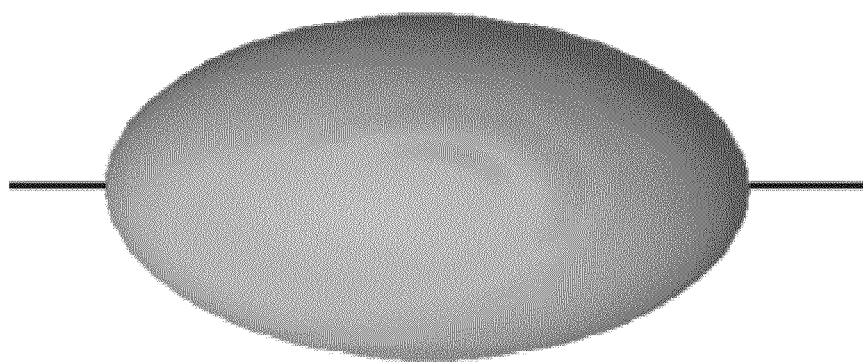
FIG. 4 is a top view of a representative tensor in accordance with embodiments of the present invention.
Figure 5A:
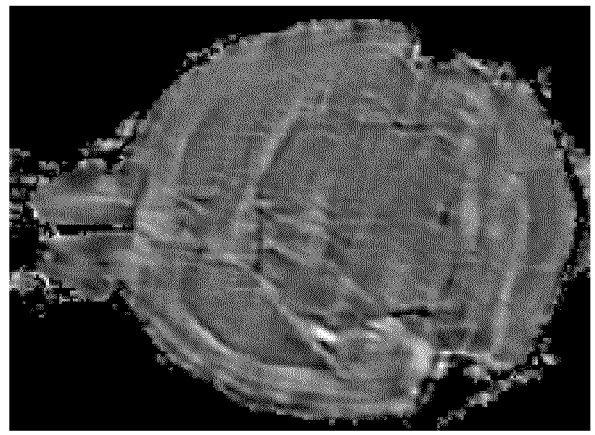
FIGS. 5A through F are an illustration of MRI images in accordance with embodiments of the present invention.
Figure 5B:
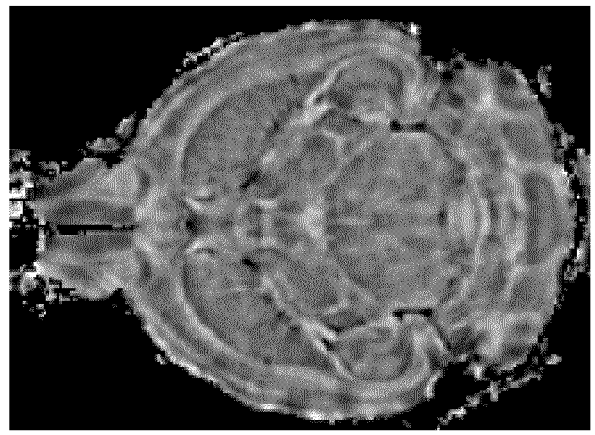
Figure 5C:
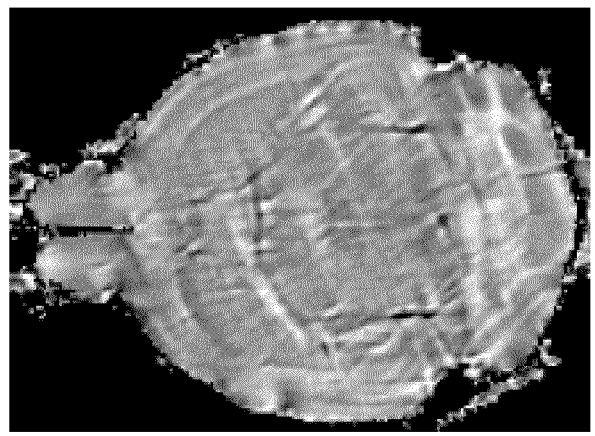
Figure 5D:
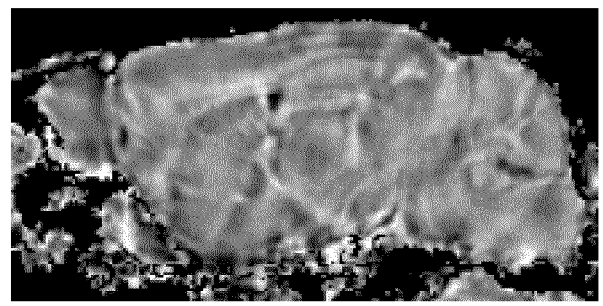
Figure 5E:
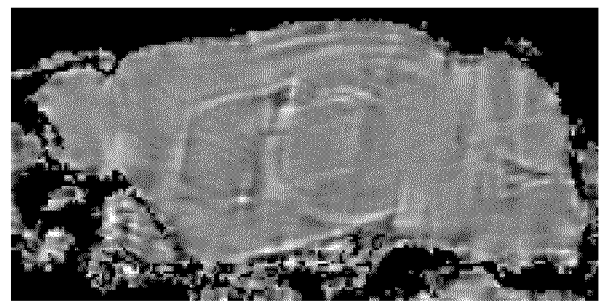
Figure 5F:
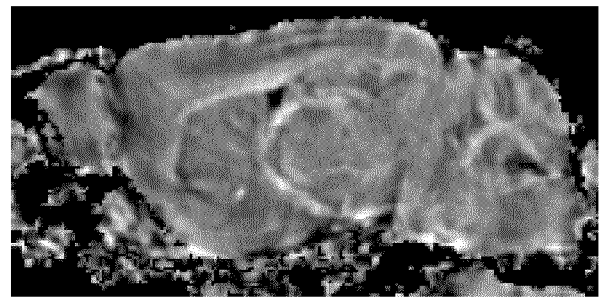
Figure 6A:
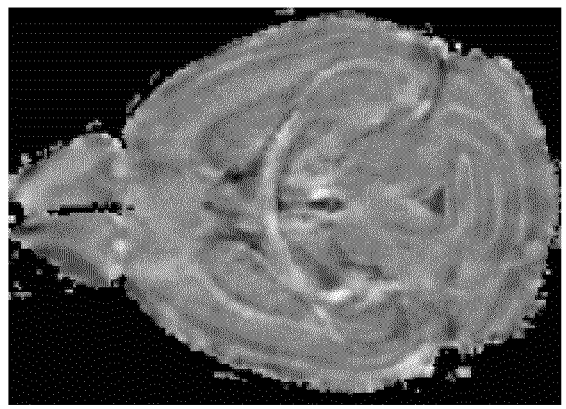
FIGS. 6A through F are an illustration of MRI images in accordance with embodiments of the present invention.
Figure 6B:
Figure 6C:
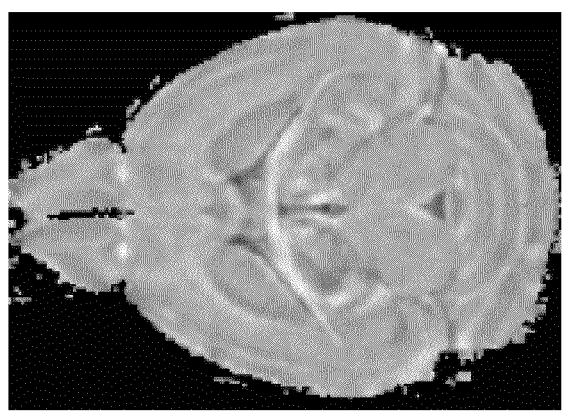
Figure 6D:
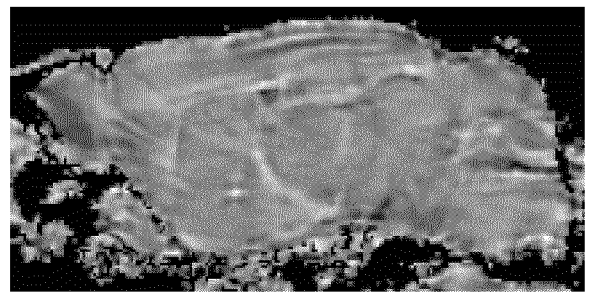
Figure 6E:
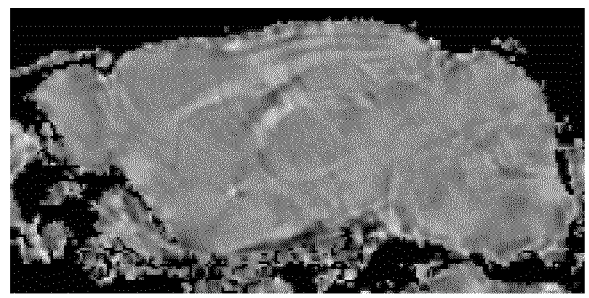
Figure 6F:
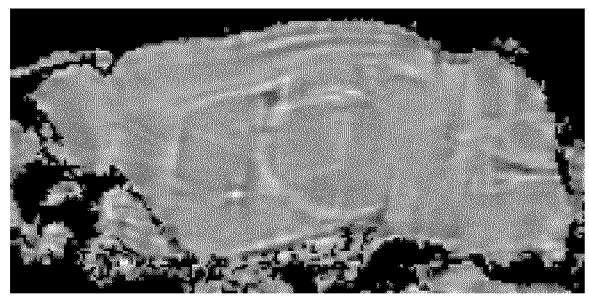

The shape of the tensor may be visualized by a susceptibility ellipsoid whose radii are defined by the principal susceptibilities. When principal susceptibilities are negative, their absolute values may be used instead or a baseline may be added. An example susceptibility ellipsoid is shown in FIG. 4. The shape of the tensor may be characterized by a shape parameter T defined as:

$$T = \frac{\ln(\chi_2/\chi_3) - \ln(\chi_1/\chi_2)}{\ln(\chi_2/\chi_3) + \ln(\chi_1/\chi_2)} \qquad [35]$$

Other scalar parameters can also be defined based on the three eigen-values.

Experimental Demonstration

Experimental Setup

In accordance with an experiment of the disclosed subject matter, to demonstrate the existence of MSA and to illustrate the proposed susceptibility tensor imaging (STI) technique, ex vivo MR microscopy was performed on mouse brains at a small-bore 7T MRI scanner.

According to the procedure, animals (adult (9-12 weeks) C57BL/6 mice [The Jackson Laboratory, Bar Harbor, Me.; Charles River, Raleigh, N.C.]) are anesthetized with Nembutal. A catheter is inserted into the left ventricle of the mouse heart. The animal is perfused with a peristaltic pump first with a mixture of 0.9% saline and ProHance (10:1, v:v) (Bracco Diagnostics, Princeton, N.J.), then with a mixture of 10% buffered formalin and ProHance (10:1, v:v). The perfused mouse brain is kept within the skull to prevent any potential damage to the brain caused by surgical removal. This fixation procedure simultaneously preserves the tissue and preferentially enhances the signal by reducing the spin lattice relaxation time. In addition, in comparison to conventional fixation techniques, the active staining technique appears to largely preserve the diffusion property of the brain tissues. For example, a mean diffusivity of $0.5 \times 10^{-3}$ mm$^2$/s has been measured for gray matter and $0.4 \times 10^{-3}$ mm$^2$/s for white matter.

Ultra-high resolution 3D SPGR images were acquired using a 7T horizontal bore magnet with shielded coil providing gradients of 160 G/cm. The imaging parameters were: matrix=$256 \times 256 \times 256$, FOV=$22 \times 22 \times 22$ mm$^3$, TE=8 ms, and TR=100 ms. All images were acquired using a 7T magnet with shielded coil providing gradients of 770 mT/m over 90 mm FOV. The system is controlled by a GE EXCITE MR imaging console. The specimen was sealed tightly inside a cylindrical tube (length 30 mm and diameter 11 mm). To allow free rotation, the tube was contained within and taped to a hollow sphere (diameter 30 mm). The sphere containing the specimen was placed inside a dual-channel mouse coil (diameter 31 mm, M2M imaging Corp, Cleveland Ohio). After each acquisition, the sphere was rotated to a different orientation and the acquisition was repeated. A total of 19 orientations were sampled that roughly cover the spherical surface evenly. To avoid-introduced frequency shifts, the same shimming currents were applied for all directions. The carrier frequency was also kept the same. Temperature was monitored through the scans and fluctuation was recorded to be below 1° C.

Orientation-Dependent AMS and AST

AMS was computed for each orientation. The computed AMS maps are then coregistered to a reference orientation. Examples of the orientation dependent AMS are shown in FIGS. 5A through F.

The AST was computed for the ex vivo mouse brain data. The three diagonal elements of the AST from a representative slice are shown in FIGS. 6A through F. The anisotropy existing in the AST is clearly evident. The anisotropy is the strongest in white matter while relatively weaker in the gray matter. The observed anisotropy is not a consequence of the tensor model. Isotropic medium may be described by a diagonal tensor with equal diagonal entries.

Figure 7B:
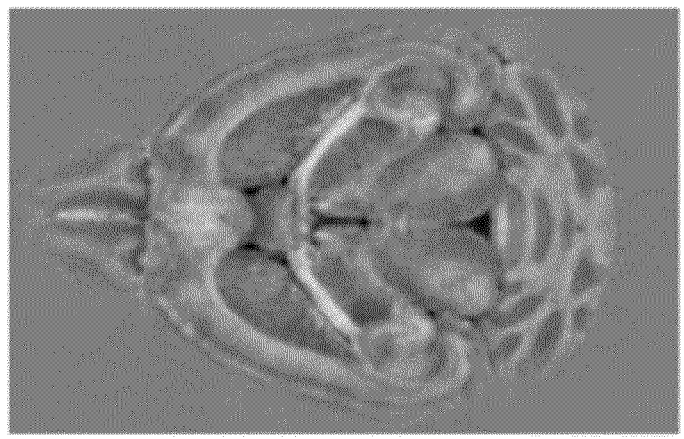
FIGS. 7A through D are an illustration of MRI images of susceptibilities in accordance with embodiments of the present invention.
Figure 7A:
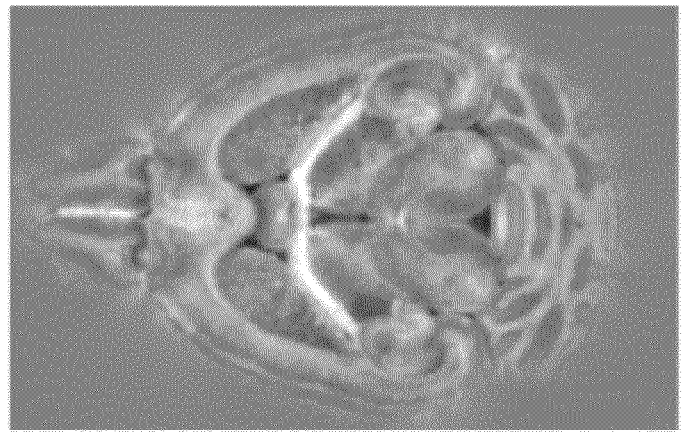
Figure 7D:
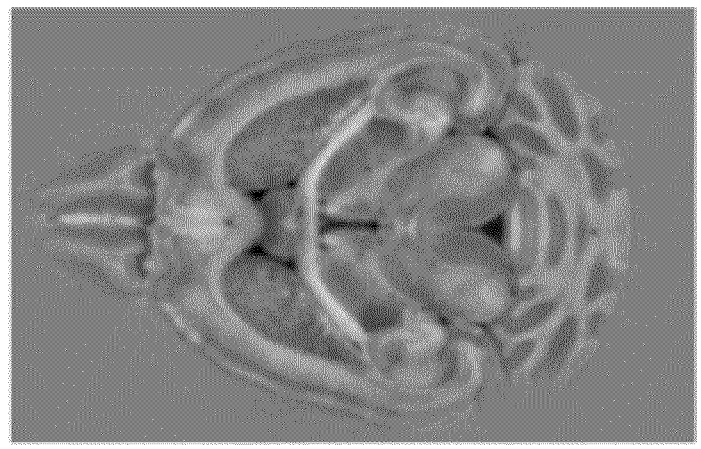
Figure 7C:
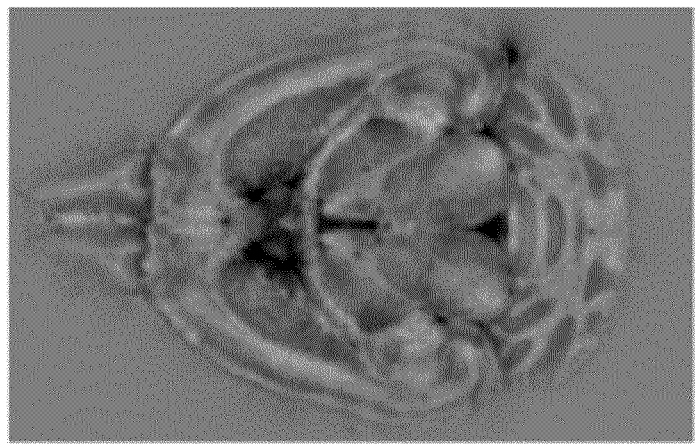
Figure 8B:
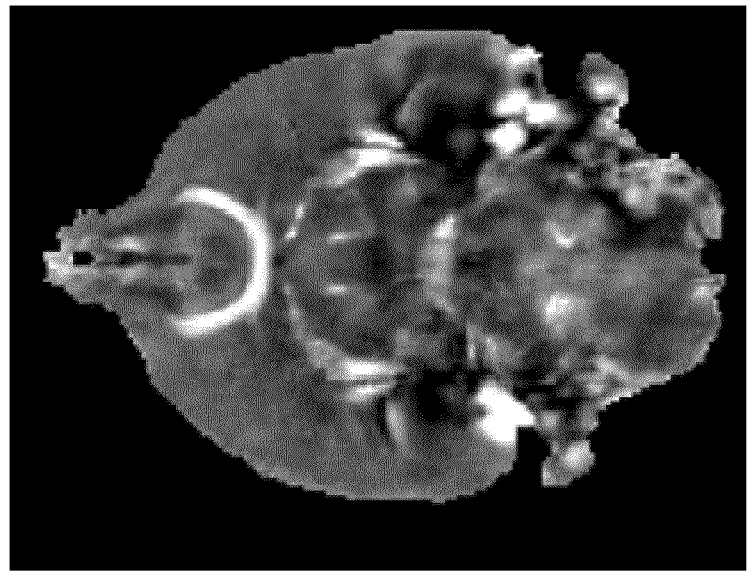
FIGS. 8A and 8B are an illustration of brain MSA in accordance with embodiments of the present invention.
Figure 8A:
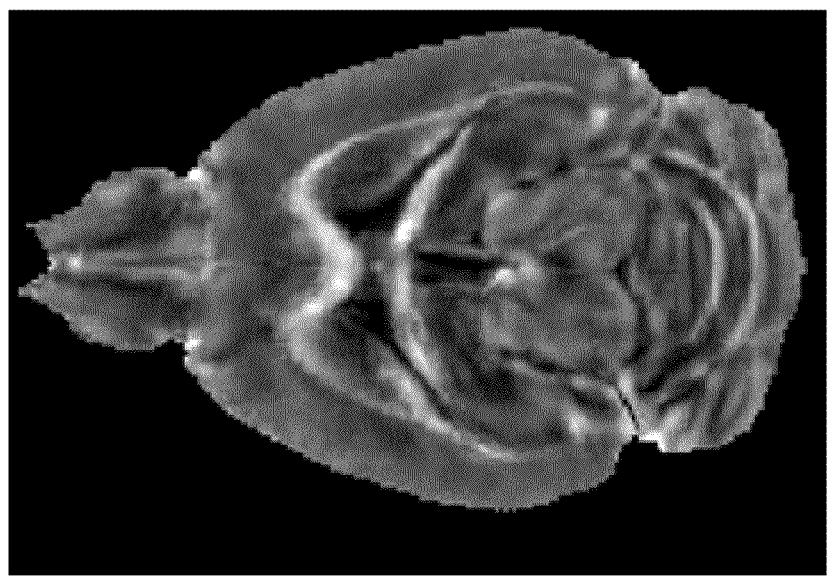

The AST may be further decomposed into three eigenvectors and three associated eigen-values. Examples of eigen-value maps are shown in FIGS. 7A through D. FSA and color-coded FSA is shown in FIGS. 7A, B, C, and D. The major eigen-vector is projected onto the plane in an example region of interest in FIGS. 8A and 8B.

Application

MSA allows for image contrast generation for non-invasive ex vivo and in vivo MRI. As one example, MSA may be acquired, analyzed, and visualized with STI. This contrast may be a result of intrinsic tissue property or may be induced by external agents. This technique may be applied in any in vivo or ex vivo MRI imaging/microscopy where the imaged subject exhibits MSA.

Tissue Contrast

Biologic tissues such as brain white and gray matter contain various amounts of iron and macromolecules. These iron and macromolecules carry an intrinsic magnetic susceptibility tensor that is determined by the iron property, the structural configuration of the macromolecules, and the dipolar coupling between different nuclei. Furthermore, once these irons and macromolecules are bonded with local tissue, the binding will enforce additional constraints on the orientation of the macromolecules thus affecting the apparent susceptibility tensor observed within one voxel. Consequently, because of tissue heterogeneity, there will be a difference between their AMS, AST, and MSA. Images may then be created by using these quantities to visualize and enhance tissue contrast. These images include a display of AMS, elements of AST, eigen-values and eigen-vectors of AST, and a combination thereof such as a magnitude image weighted by AMS. Tissue structural changes caused by tumor, stroke, traumatic injury, and iron-content changes caused by developmental iron deficiency and aging will then manifest in the changes of those quantities.

Brain Connectivity and Tractography

Currently, diffusion tensor MRI is a non-invasive method for visualizing whole brain white matter fiber tracts in vivo. DTI fiber tractography may be used for in vivo mapping of brain neural networks and may be used in the fields of diagnostic radiology, neuroscience, psychology and psychiatry. The basic assumption of DTI fiber tractography is that the most preferable diffusion orientation of water molecules inside white matter is along the fibers. Therefore, by following the major eigenvector direction, one is able to trace white matter fibers in three dimensions inside the whole brain. DTI tractography has so far faced three main challenges. Currently, it is thought that there is no other in vivo tracking method that may be used to validate DTI tractography. DTI tractography is ineffective of resolving multiple fiber orientations within one voxel. Third, DTI is extremely susceptible to motion and off-resonance artifacts. The image quality and spatial resolution of DTI as a result has so far been severely limited.

In addition, DTI has encountered significant difficulties at ultra-high field strength (7T and above). Although ultra high field offers stronger raw signal strength, this strength has been so far difficult if not impossible for DWI/DTI to take advantage of. Many challenges still need to be overcome before improved DWI/DTI image quality may be obtained at 7T. The difficulties include: more rapid T2 and T2* decay that negates the gain of raw signal strength; high specific absorption rate (SAR) that limits slice coverage of the brain and causes safety concern; severe inhomogeneous B1-field that induces additional signal-to-noise (SNR) loss; and severe off-resonance artifacts that create severe geometrical distortion for echo-planner-imaging (EPI) and blurring for spiral imaging. The current DWI/DTI quality at 7T is still significantly below that of 3T. The development in this area has been limited to implementing DWI/DTI at ultra-high field. Single shot EPI, the most-widely used technique for DWI acquisition, has been impractical at 7T and higher, even at the typical $2 \times 2$ mm$^2$ resolution. Until more sophisticated technology is developed to address the aforementioned challenges, routine application of DWI/DTI at 7T will remain impractical.

More importantly, DTI primarily sensitizes to geometrical changes and offers few insights on tissue specificity. STI may offer a number of important benefits that will significantly enhance pediatric neuroimaging, such as: new insights on white matter architecture complimenting and potentially cross-validating DTI results, superior resolution ($0.4 \times 0.4 \times 1.0$ mm$^3$), safer and significantly smaller specific absorption rate (SAR), inherent advantage at high and ultra-high fields where susceptibility effect is amplified, compatibility with ultra-short T2 species and specific information on tissue composition of iron and proteins that are important for brain development.

The orientation information offered by STI may be used to reconstruct white matter fiber pathways, thus providing a much-needed second in vivo method for mapping brain white matter fiber pathways.

Susceptibility Tensor Spectroscopic Imaging (STSI)

Within an image volume, each voxel contains an ensemble of microscopic susceptibility tensors. The measured AST is an ensemble average of all microscopic susceptibility tensors. Each microscopic tensor is an intrinsic property of the molecules within the voxel. In a solution form, the orientation information of the microscopic tensor is averaged out if molecules are orienting randomly or are tumbling quickly. However, in an ordered structure such as brain tissue and especially the white matter, the rotational mobility of those molecules is restricted. Consequently, there will be some residual orientation information within each voxel. The signal observed in a typical proton MRI experiment is primarily from water molecules due to their relatively long T2 and T2* values compared to those of macromolecules. Both free water protons and protons exchanged from macromolecules are included. Diffusion of water molecules within brain tissue, especially within white matter, is anisotropic. Therefore, this anisotropic diffusion process cannot average out the surrounding anisotropic susceptibility tensor. As a result, the residual orientation information will manifest as a frequency spectrum that may be obtained in a spectroscopic imaging experiment. The frequency range of this residual dipole field is typically within 0.1 ppm, much smaller than that of NAA (2 ppm) for example. The spectrum distribution may be expressed as:

$$\omega = \gamma B_0 \int_\theta \int_\varphi p(\theta, \varphi) R_\chi^T(\theta, \varphi) R(\theta, \varphi) \, d\theta \, d\varphi \quad [36]$$

Here, $p(\theta,\phi)$ is the ODF of the molecular orientation; $\chi$ is the molecular susceptibility tensor expressed in the molecular coordinate; and R is the rotation matrix between the laboratory frame and the molecular frame. Once the spectrum is obtained, the preferable orientation of the molecules may be estimated.

Alternatively, susceptibility tensor spectroscopic imaging (STSI) can also be conducted on other nuclei that exhibit NMR signals. For example, direct STSI of 13C, 15N, 31P and 19F would provide a more direct examination of the molecular susceptibility tensor. Such examination would not depend on the diffusion interaction between water protons and the microscopic susceptibility tensor. The signal gain of hyperpolarized nuclei such hyperpolarized 13C will aid the detection the MSA greatly.

Molecular Imaging

Molecular imaging is another important area of application for the methodology developed here and the interaction mechanism described by this invention between water proton diffusion and microscopic susceptibility. The method may be used to guide the design of molecular contrast agent and may be used to detect small concentrations of these agents once injected into the tissue. Specific exogenous contrast agents may be designed to enhance its MSA by manipulating its structure and by adding frequency-shifting atoms. These contrast molecules may be designed to allow certain preferable binding configurations and orientations with tissue macromolecules thus to further enhance local MSA. This invention provides the methodology to further detect and enhance the tissue-specific and pathology-specific anisotropic shift effect. Imaging of this class of molecular contrast agent will not just simply rely on T1 or T2* effects. Rather, it will rely on the anisotropic magnetic field generated by these agents.

In accordance with embodiments of the present invention, an MRI system as disclosed herein may be implemented on any computing device suitable for implementing a transaction.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter situation scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or diagrams of methods, apparatus (systems) and computer program products according to embodiments of the invention. For example, aspects of the present invention are described with reference to the diagram of FIG. 1 and the flowchart of FIG. 2. It will be understood that each block of the flowchart illustrations and/or diagrams, and combinations of blocks in the flowchart illustrations and/or diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for magnetic resonance imaging (MRI) comprising:
    using an MRI system to acquire susceptibility tensor data of an object, the susceptibility tensor data being rank 2 or higher and including a plurality of voxels;
    determining orientations of the voxels;
    determining whether each of the voxels has an eigenvalue greater than a predetermined magnitude;
    identifying adjacent voxels that each have an eigenvalue greater than the predetermined magnitude;
    for each identified adjacent voxel, determining whether an angle between eigenvectors of the identified adjacent voxels is less than a predetermined angle value; and
    generating an image based on the orientations of the voxels for depicting a characteristic of the object, wherein generating an image comprises generating an image that depicts one or more lines extending between the identified adjacent voxels in which the angle between eigenvectors is less than the predetermined angle value.

2. The method of claim 1, wherein using an MRI system comprises using the MRI system to apply a magnetic field to the object.

3. The method of claim 1, wherein using an MRI system comprises using the MRI system to acquire susceptibility tensor data of the object at a plurality of orientations of the object relative to a magnetic field generated by the MRI system.

4. The method of claim 1, comprising determining one of vector components, eigenvalue decomposition, and invariant functions of susceptibility tensors of the voxels, and
    wherein generating an image comprises generating the image based on the one of vector components, eigenvalue decomposition, and invariant functions of the susceptibility tensors.

5. The method of claim 1, wherein generating an image comprises generating the image based on the susceptibility tensors for depicting a tissue characteristic of the object.

6. The method of claim 1, wherein determining orientations of the voxels comprises determining apparent susceptibility tensors of the voxels.

7. The method of claim 1, wherein determining orientations of the voxels comprises determining an orientation distribution function of the voxels, the orientation distribution function being susceptibility as a function of magnetic field or object orientation.

8. The method of claim 1, wherein the object includes a fiber structure, and
wherein the method comprises identifying a set of voxels corresponding to the fiber structure based on one of magnetic susceptibility tensors and resonance frequency shift of the set of voxels.

9. A magnetic resonance imaging (MRI) system, comprising:
an MRI device configured to acquire susceptibility tensor data of an object, the susceptibility tensor data being rank 2 or higher and including a plurality of voxels; and
an image generator configured to:
determine orientations of the voxels;
determine whether each of the voxels has an eigenvalue greater than a predetermined magnitude;
identify adjacent voxels that each have an eigenvalue greater than the predetermined magnitude;
for each identified adjacent voxel, determine whether an angle between eigenvectors of the identified adjacent voxels is less than a predetermined angle value;
control a display to generate an image based on the orientations of the voxels for depicting a characteristic of the object; and
control the display to generate an image that depicts one or more lines extending between the identified adjacent voxels in which the angle between eigenvectors is less than the predetermined angle value.

10. The system of claim 9, wherein the MRI device is configured to acquire susceptibility tensor data of the object at a plurality of orientations of the object relative to a magnetic field generated by the MRI system.

11. The system of claim 9, wherein the image generator is configured to:
determine one of vector components, eigenvalue decomposition, and invariant functions of susceptibility tensors of the voxels; and
control the display to generate an image based on the one of vector components, eigenvalue decomposition, and invariant functions of the susceptibility tensors.

12. The system of claim 9, wherein the image generator is configured to control the display to generate an image based on the susceptibility tensors for depicting a tissue characteristic of the object.

13. The system of claim 9, wherein the image generator is configured to determine one of a magnetic susceptibility tensor and an apparent susceptibility tensor of the voxels.

14. The system of claim 9, wherein the image generator is configured to determine an orientation distribution function of the voxels.

15. The system of claim 9, wherein the object includes a fiber structure, and
wherein the image generator is configured to identify a set of voxels corresponding to the fiber structure based on one of magnetic susceptibility tensor and resonance frequency shift of the set of voxels.

16. A computer program product for controlling a magnetic resonance imaging (MRI) system, said computer program product comprising:
a non-transitory computer readable storage medium having computer readable program code embodied therewith, the computer readable program code comprising:
computer readable program code configured to use an MRI device to acquire susceptibility tensor data of an object, the susceptibility tensor data being rank 2 or higher and including a plurality of voxels;
computer readable program code configured to determine orientations of the voxels;
computer readable program code configured to determine whether each of the voxels has an eigenvalue greater than a predetermined magnitude;
computer readable program code configured to identify adjacent voxels that each have an eigenvalue greater than the predetermined magnitude;
computer readable program code configured to, for each identified adjacent voxel, determine whether an angle between eigenvectors of the identified adjacent voxels is less than a predetermined angle value;
computer readable program code configured to control a display to generate an image based on the orientations of the voxels for depicting a characteristic of the object; and
computer readable program code configured to control the display to generate an image that depicts one or more lines extending between the identified adjacent voxels in which the angle between eigenvectors is less than the predetermined angle value.

17. A method for magnetic resonance imaging (MRI) comprising:
using an MRI system to acquire susceptibility tensor data of an object, the susceptibility tensor data being rank 2 or higher and including a plurality of voxels;
determining orientations of the voxels;
determining whether an angle between orientations of adjacent voxels is less than a predetermined angle value; and
generating an image based on the orientations of the voxels for depicting a characteristic of the object, wherein generating an image comprises generating an image that depicts one or more lines extending between the adjacent voxels in which the angle is less than the predetermined angle value.

18. A magnetic resonance imaging (MRI) system, comprising:
an MRI device configured to acquire susceptibility tensor data of an object, the susceptibility tensor data being rank 2 or higher and including a plurality of voxels; and
an image generator configured to:
determine orientations of the voxels;
determine whether an angle between orientations of adjacent voxels is less than a predetermined angle value;
control a display to generate an image based on the orientations of the voxels for depicting a characteristic of the object; and
control the display to generate an image depicting a characteristic of the object comprises generating an image that depicts one or more lines extending between the adjacent voxels in which the angle is less than the predetermined angle value.

19. A computer program product for controlling a magnetic resonance imaging (MRI) system, said computer program product comprising:
a non-transitory computer readable storage medium having computer readable program code embodied therewith, the computer readable program code comprising:
computer readable program code configured to acquire susceptibility tensor data of an object, the susceptibility tensor data being rank 2 or higher and including a plurality of voxels;
computer readable program code configured to determine orientations of the voxels;
computer readable program code configured to determine whether an angle between orientations of adjacent voxels is less than a predetermined angle value;

computer readable program code configured to control a display to generate an image based on the orientations of the voxels for depicting a characteristic of the object; and computer readable program code configured to control the display to generate an image depicting a characteristic of the object comprises generating an image that depicts one or more lines extending between the adjacent voxels in which the angle is less than the predetermined angle value.

* * * * *